United States Patent [19]

McLaughlin et al.

[11] Patent Number: 5,984,887
[45] Date of Patent: *Nov. 16, 1999

[54] PHOTOPHERESIS TREATMENT OF LEUKOCYTES

[75] Inventors: Susan N. McLaughlin, Phoenixville; Bruce C. Stouch, Newtown Square, both of Pa.; Jerome B. Zeldis, Princeton, N.J.

[73] Assignee: Therakos, Inc., Exton, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/832,322

[22] Filed: Mar. 26, 1997

Related U.S. Application Data

[60] Provisional application No. 60/014,269, Mar. 29, 1996, and provisional application No. 60/029,893, Nov. 8, 1996.

[51] Int. Cl.⁶ .................................................. A61M 37/00
[52] U.S. Cl. ........................................................... 604/4
[58] Field of Search ........................... 604/4–6; 607/97

[56] References Cited

U.S. PATENT DOCUMENTS

| 298,279 | 10/1884 | Lee et al. . |
| 298,567 | 11/1884 | Morris . |
| D. 299,531 | 1/1989 | Troutner et al. . |
| 299,953 | 2/1884 | King et al. . |
| 4,196,281 | 4/1980 | Hearst et al. . |
| 4,321,919 | 3/1982 | Edelson . |
| 4,398,906 | 8/1983 | Edelson . |
| 4,428,744 | 1/1984 | Edelson . |
| 4,452,811 | 6/1984 | della Ville . |
| 4,464,166 | 8/1984 | Edelson . |
| 4,464,354 | 8/1984 | Bisagni et al. . |
| 4,465,691 | 8/1984 | Bisagni et al. . |
| 4,568,328 | 2/1986 | King . |
| 4,573,960 | 3/1986 | Goss . |
| 4,573,961 | 3/1986 | King . |
| 4,573,962 | 3/1986 | Troutner . |
| 4,578,056 | 3/1986 | King et al. . |
| 4,596,547 | 6/1986 | Troutner . |
| 4,612,007 | 9/1986 | Edelson . |
| 4,613,322 | 9/1986 | Edelson . |
| 4,623,328 | 11/1986 | Hartranft . |
| 4,643,710 | 2/1987 | Troutner . |
| 4,681,568 | 7/1987 | Troutner . |
| 4,683,889 | 8/1987 | Edelson . |
| 4,684,521 | 8/1987 | Wdelson . |
| 4,687,464 | 8/1987 | Troutner . |
| 4,692,138 | 9/1987 | Troutner et al. . |
| 4,693,981 | 9/1987 | Wiesehahn et al. . |
| 4,705,498 | 11/1987 | Goss . |

(List continued on next page.)

FOREIGN PATENT DOCUMENTS

| 88302660 | 3/1988 | European Pat. Off. . |
| WO93/14791 | 1/1993 | WIPO . |
| WO95/03814 | 7/1994 | WIPO . |

OTHER PUBLICATIONS

Richard Edelson et al. "Treatment of Cutaneous T–cell Lymphoma By Extracorporeal Photochemotherapy" New England Journal of Medicine 316:297–303 (Feb. 5, 1987).

Marglis–Nunno et al."Elimination of Potential Mutagenicity in Plantlet Concentrates that are virally Inactivate with Psoralens and Ultraviolet A Light" Transformation 1985:pp. 855–862.

(List continued on next page.)

Primary Examiner—John G. Weiss
Assistant Examiner—Ki Yong O
Attorney, Agent, or Firm—John W. Wallen, III

[57] ABSTRACT

A method of treating infections of mononuclear blood cells, other than retroviral infections, is disclosed. A method of modulating the function of monocytes is also disclosed. The method involves the treatment of a patient's blood with a photoactivatable compound followed by ultra violet light-activation of the photoactivatable compound. The blood treated as such is returned to the patient in a process known as extracorporeal photopheresis. Monocyte function is modulated by this treatment.

9 Claims, 6 Drawing Sheets

U.S. PATENT DOCUMENTS

| | | |
|---|---|---|
| 4,708,715 | 11/1987 | Troutner et al. . |
| 4,726,949 | 2/1988 | Miripol et al. . |
| 4,727,027 | 2/1988 | Wiesehahn et al. ............... 435/173 |
| 4,737,140 | 4/1988 | Lee et al. . |
| 4,748,120 | 5/1988 | Wiesehahn ............................ 435/173 |
| 4,838,852 | 6/1989 | Edelson et al. . |
| 4,866,282 | 9/1989 | Miripol et al. . |
| 4,897,789 | 1/1990 | King et al. . |
| 4,921,473 | 5/1990 | Lee et al. . |
| 4,952,812 | 8/1990 | Miripol et al. . |
| 4,960,408 | 10/1990 | Klainer et al. . |
| 4,999,375 | 3/1991 | Bachynsky et al. . |
| 5,030,200 | 7/1991 | Judy et al. . |
| 5,176,921 | 1/1993 | Wiesehahn et al. . |
| 5,216,176 | 6/1993 | Heindel et al. . |
| 5,288,605 | 2/1994 | Lin et al. . |
| 5,356,929 | 10/1994 | Heindel et al. . |
| 5,360,734 | 11/1994 | Cgaonab et al. . |
| 5,399,719 | 3/1995 | Wollowitz et al. ............... 549/282 |
| 5,459,030 | 10/1995 | Lin et al. . |
| 5,482,828 | 1/1996 | Lin et al. . |
| 5,651,993 | 7/1997 | Edelson et al. . |

OTHER PUBLICATIONS

Hoofnagle et al. Treatment of chronic Non–A, Non–B Hepatitis with Recombinant Human Alpha interferon New England Journal of Medicine vol. 315 No. 25 pp. 1575–1578.

Davis et al. "Treatment of Chronic Hepatitis C with Recombinant Interferon Alfa" New England Journal of Medicine vol. 321 No. 22 pp. 1501–1505.

DiBisceglie et al. "Recombinant Interferon Alfa Therapy for Chronic Hepatitis C" New England Journal of Medicine vol. 321 No. 22 pp. 1506–1510.

Farci et al "A Long–term Study of Hepitatis C Virus Replication in non–A, Non–B Hepatitis" New England Journal of Medicine vol. 325 No. 2 pp. 98–103.

Shindo et al. "Decrease in Serum Hepatitis C Viral RNA during Alpha–Interferon Therapy for Chronic Hepatitis C" Annals of Internal Medicine vol. 115 No. 9 pp. 701–704.

"High Dose Interferon Alfa–2A for the Treatment of Chronic Hepatitis C" The Annals of Pharmacotherapy 1994 Mar. vol. 28 pp. 341–342.

M. Gomez–Rubio et al. "Prolonged Treatment (18 months) of Chronic Hepatitis C with Recombinant α–Interferon in comparison with a control group" Journal of Hepatology, 1990:11:S63–S67.

Saez–Royuela et al. "High Doses of Recombinant α–Interferon or γ–Interferon for Chronic Hepatitis C: A Randomized, Controlled Trial" Hepatology 1991; 13:No. 2 327–331.

Nakano et al. "Comparative Study of Clinical, Histological, and Immunologics Responses to Interferon Therapy in Type Non–A, Non–B, and Type B Chronic Hepatitis" The American Journal of Gastroenterology vol. 85; No. 1.1990.

Haysahi et al. "Improvement of Serum Aminotransferase Levels after Phlebotomy in Patients with chronic Active Hepatitis C and Excess Hepatic Iron" The American Journal of Gastroenterology vol. 89; No. 7.1994 pp. 986–988.

Ljunggren et al. "Plasma Levels of 8 Methoxypsoralen Determined by High–Pressure Liquid Chromatography in Psoriatic Patients Ingesting Drug from Two Manufacturers" The Journal of Investigative Dermatology, vol. 74, No. 1 pp. 59–62.

Christer T. Jansen et al. "Inter–and Intraindividual Variations in Serum Methoxsalen Levels During Repeated Oral Exposure" Therapeutic Research vol. 33, No. 2 pp. 258–264.

Michael J. Clemens et al. "Regulation of Cell Proliferation and Differentiation by Interferons" Bronchena J. (1985) 226, 345–360.

Witter et al. "Efffects of Prednisone, Aspirin, and Acetaminophen on an in vivo biologic response to interferon in humans" Clin Pharmacol Ther Aug. 1988 pp. 239–243.

Alain H. Rook, et al. "Combined Therapy for Sezary Syndrome With Extracorporeal Photochemotherapy and Low–Dose Interferon Alfa Therapy" Arch Dermatol. 1991;127: pp. 1535–1540.

Alain H. Rook, et al. "Treatment of Automimmune Disease with Extracorporeal Photochemotherapy: Pemphigus Vulgaris" The Yale Journal of Biology and Medicine 62 (1989). 647–652.

Barr et al. "Immunomodulation with photopheresis: Clinical Results of the Multi–Center Cardiac Transplantation Study" Study supported by Therakos, A Johnson & Johnson Company.

Costanzo–Nordin et al. "Successful Treatment of Heart Transplant Rejection with Photopheresis" Transplantation vol. 53, 808–815, No. 4 Apr. 1992.

Meiser et al., Reduction of the Incidence of rejection by Adjunct Immunosuppression with Photochemotherapy After Heart Transplantation Transplantation vol. 57 563–566 No. 4 Feb. 1994.

Vowels et al. "Extracorporeal Photochemotherapy Induces the Production of Tumor Necrosis Factor–α by Monocytes: Implications for the Treatment of Cutaneous T–ell Lymphoma and Systemic Sclerosis" The Journal of Investigative Dermatology, Inc. vol. 98:686–692, 1992.

Gil et al. Hepatic and Extrahepatic HCV RNA Strands in Chronic Hepatitis C: Different Patterns of Respons to Interferon Treatment Hepatology 1993; 18, 1050–1054.

Qian et al. "Replication of hepatitis C Virus in peripheral blood mononuclear cells" Journal of Hepatology 1992;16:380–383.

Elcanor C. Mandoza et al. "Decreased Phorbol Myristate Acetate–Induced Release of Tumor Necrosis Factor–α and Interleukin–1β from Peripheral Blood Monocytes of Patients Chronically Infected with Hepatitis C Virus" Journal of Infectious Disease 1996 vol. 174 pp. 42–44.

Zignego et al. "Infection of peripheral mononuclear blood cells by hepatitis C Virus" Journal of Hepathology, 1992;15:382–386.

"Mutsunori Shirai et al. "Introduction of Cytotoxic T Cells to a Cross–Reactive Epitope in the Hepatitis C. Virus Nonstructural RNA polymerase–Like Protein" Journal of Virology, Jul. 1992;pp. 4098–4106.

Amy J. Weiner et al. "Evidence for immune selection of hepatitis C virus (HCV) putative enveolpe glycoprotein variants: Potential role in chronic HCV infections" Proc. Natl. Acad. Sci. USA vol. 89 pp. 3468–3472.

Shimizu et al. "Early events in hepatitis C. Virus infection of chimpanzees" Proc. Natl. Acad. Sci. USA 87 pp. 6441–6444.

J. A. Garson et al. "Enhanced detection by PCR of hepatitis C virus RNA" The Lancet Oct. 6, 1990 p. 878.

P. Simmonds et al. "Classification of hepatitis C virus into six major genotypes and a series of subtypes by phylogenetic analysis of the NS–5 region" Journal of General Virology (1993). 74 2391–2399.

Houghton et al. "Monecular Biology of the Hepatitis C Virues: Implications for Diagnosis, Development and Control of Viral Disease" Hepatology vol. 14, No. 2 1991 pp. 381–388.

Choo et al. "Genetic organization and diversity of the hepatitis C virus" Proc. Natl. Acad. Sci. USA vol. 88, pp. 2451–2455.

Choo et al. "Isolation of a cDNA Clone Derived from a Blood Bone Non–A, Non–B Viral Hepatitis Genome".

Ronald L. Koretz et al. "Non–A, Non–B Posttransfusion Hepatitis A Decade Later" Gastroenterology 1985:88:1251–4.

Jules L. Dienstag Non–A, Non–B Hepatitis, I. Recognition, Epidemiology, and Clinical Features Gastroenterology vol. 85. No. 2.

Flavio Rossetti, et al. "Extracorporeal Photochemotherapy as single therapy for extensive, Cutaneous, Chronic Graft–versus–Host Disease" Transplantation vol. 59 No. 1 pp. 150–151.

"American Liver Foundation" Progress, 1994–95, vol. 16 pp. 1–12.

Alain H. Rook, MD et al. "Treatment of Systemic Sclerosis With Extracorporeal Photochemotherapy" Archives of Dermatology 1992;128:337–346.

Malawista et al. "Treatment of Rheumatoid Arthritis by Extracorporeal Photochemotherapy" Arthritis and Rheumatism, vol. 34, No. 6 pp. 646–654.

Richard Edelson et al. "Treatment of Cutaneous T–Cell Lymphoma by Extracorporeal Photochemotherapy" New England Journal of Medicine 316:297–304.

Richard Edelson et al. "Photopheresis: a Clinocally Relevant Immunobiologic Response Modifier"Dept. of Dermatology Yale Univ. School of Medicine.

Grass et al. "Inactivation of Leukocytes in Platelet Concentrates by Photochemical Treatment with Psoralen Plus UVA" The American Society of Hematology. Blood. vol. 91, No. 6 pp. 2180–2188.

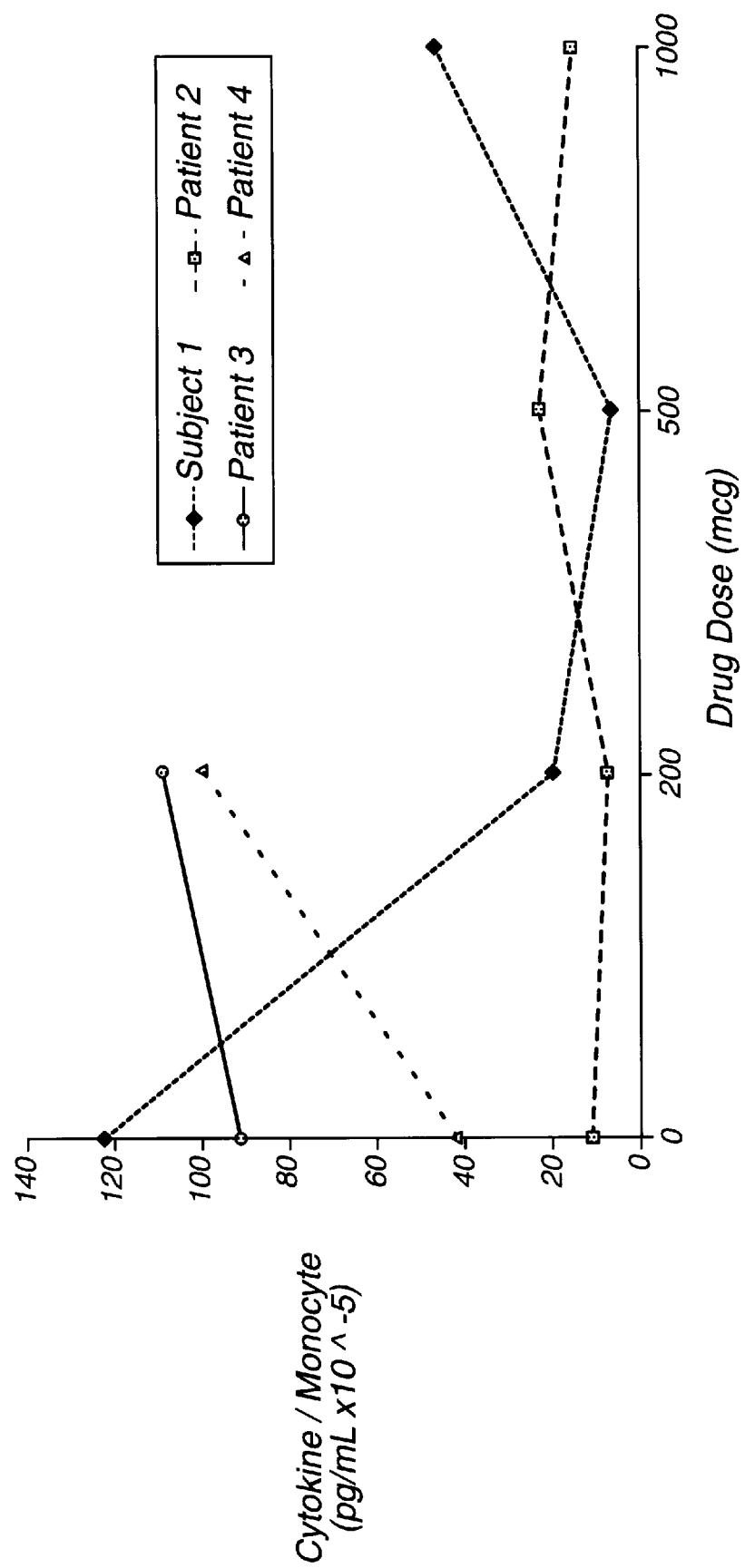

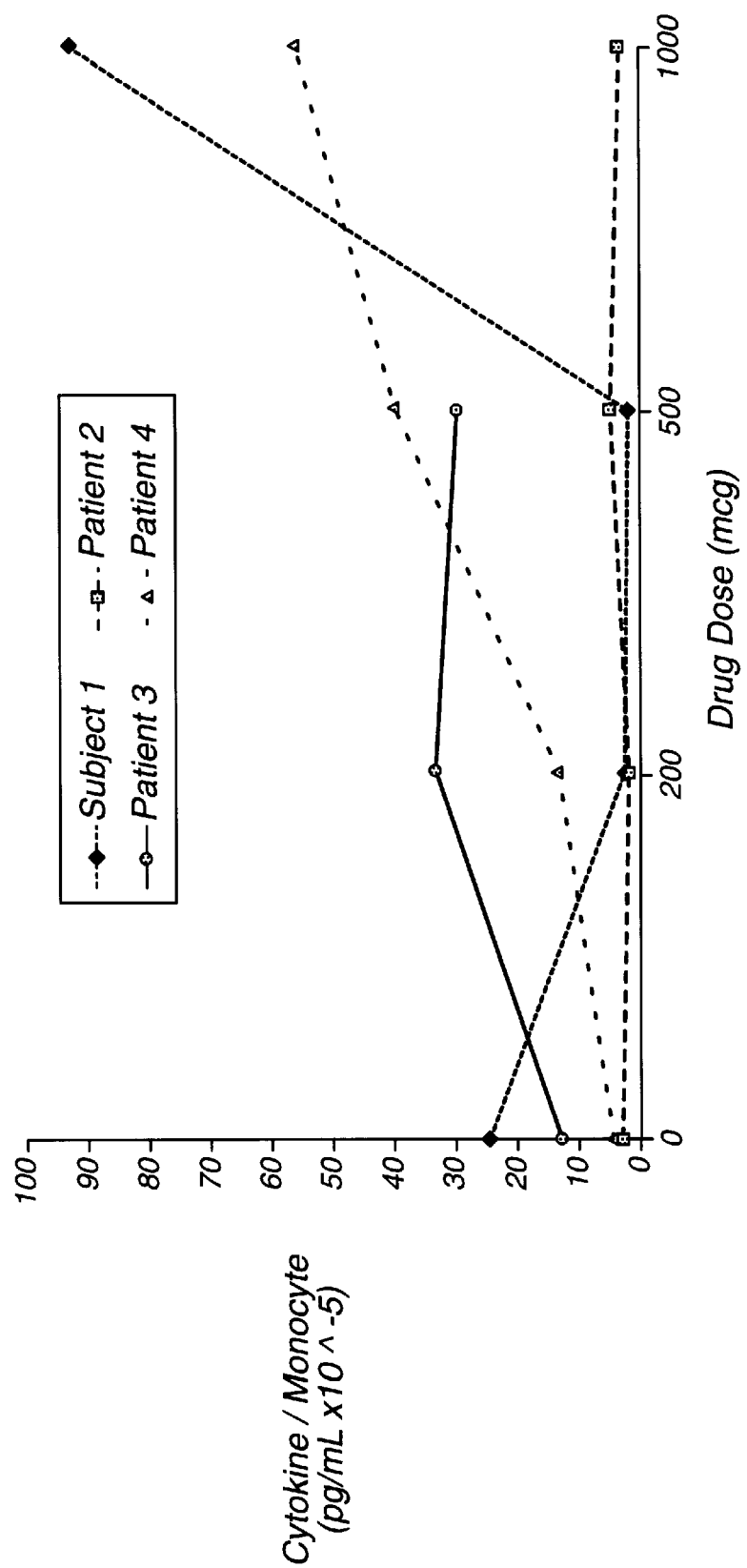

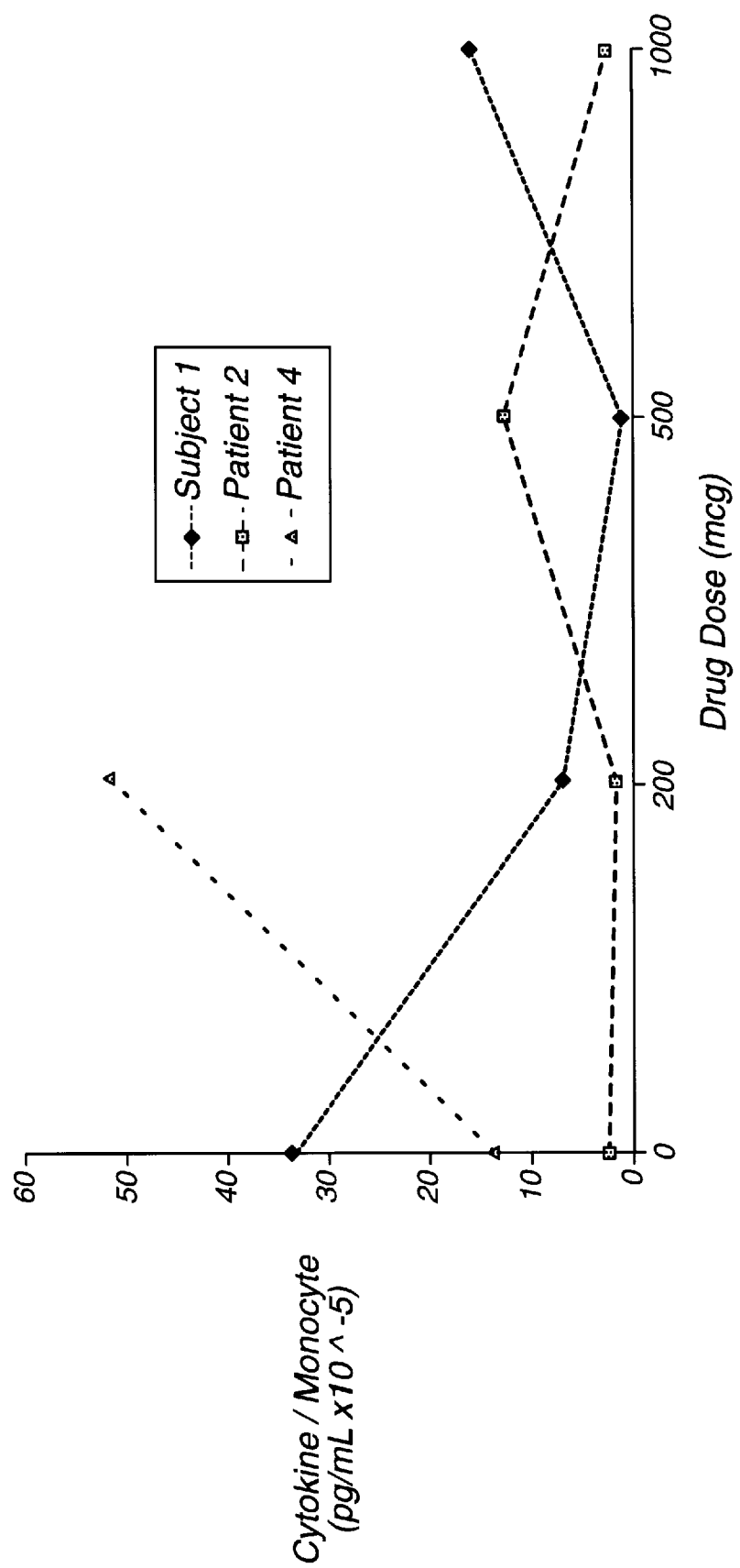

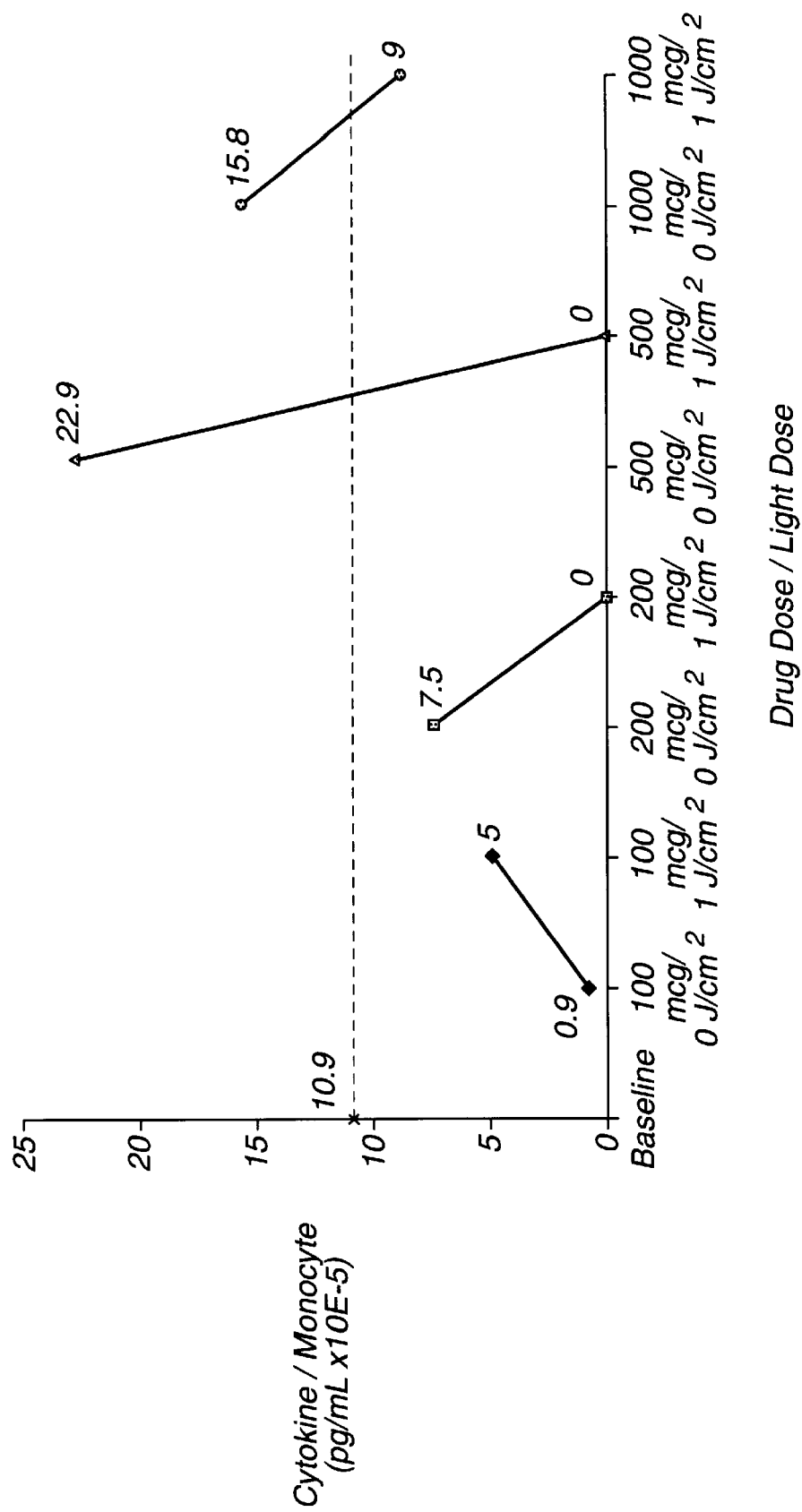

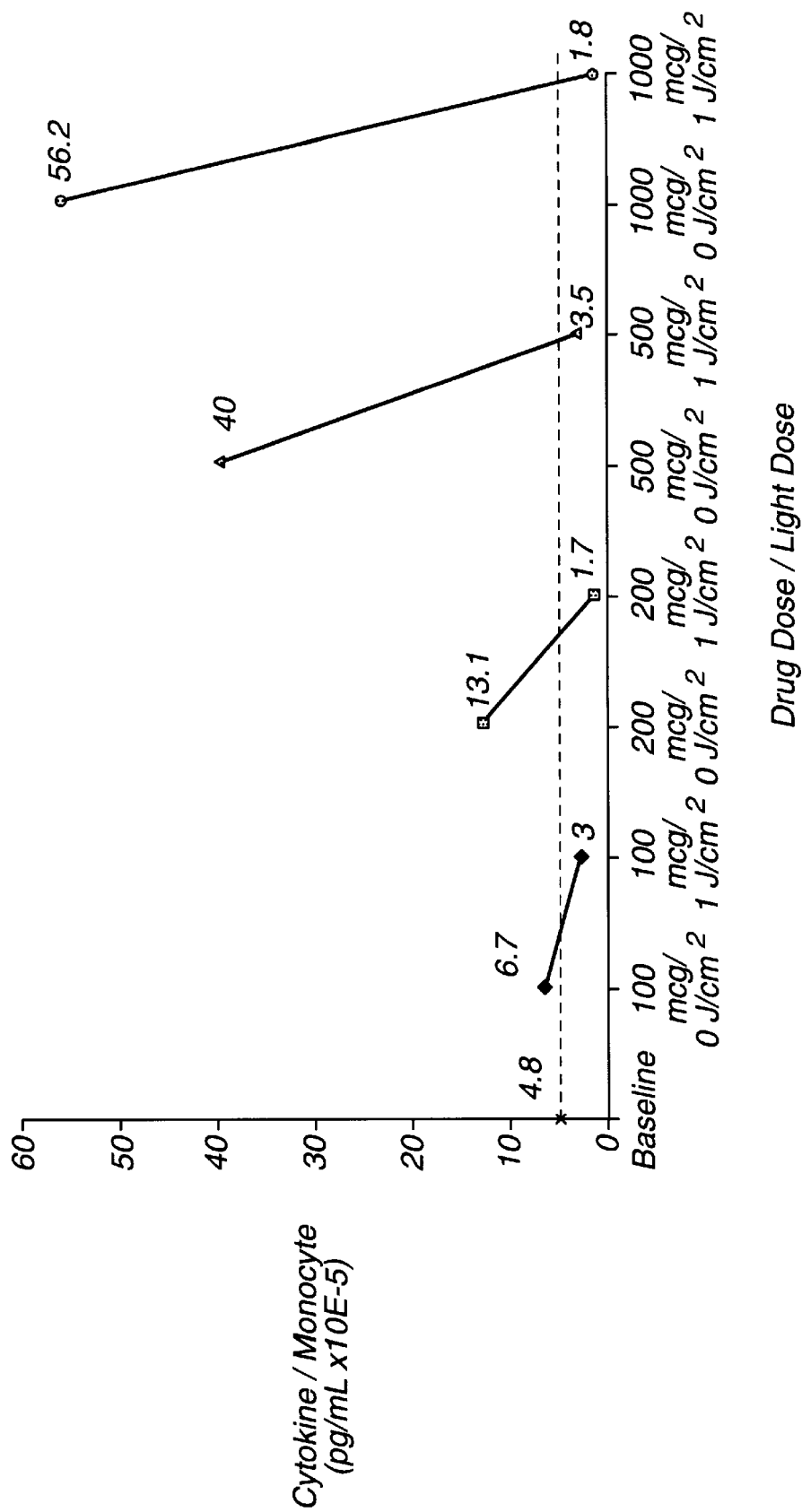

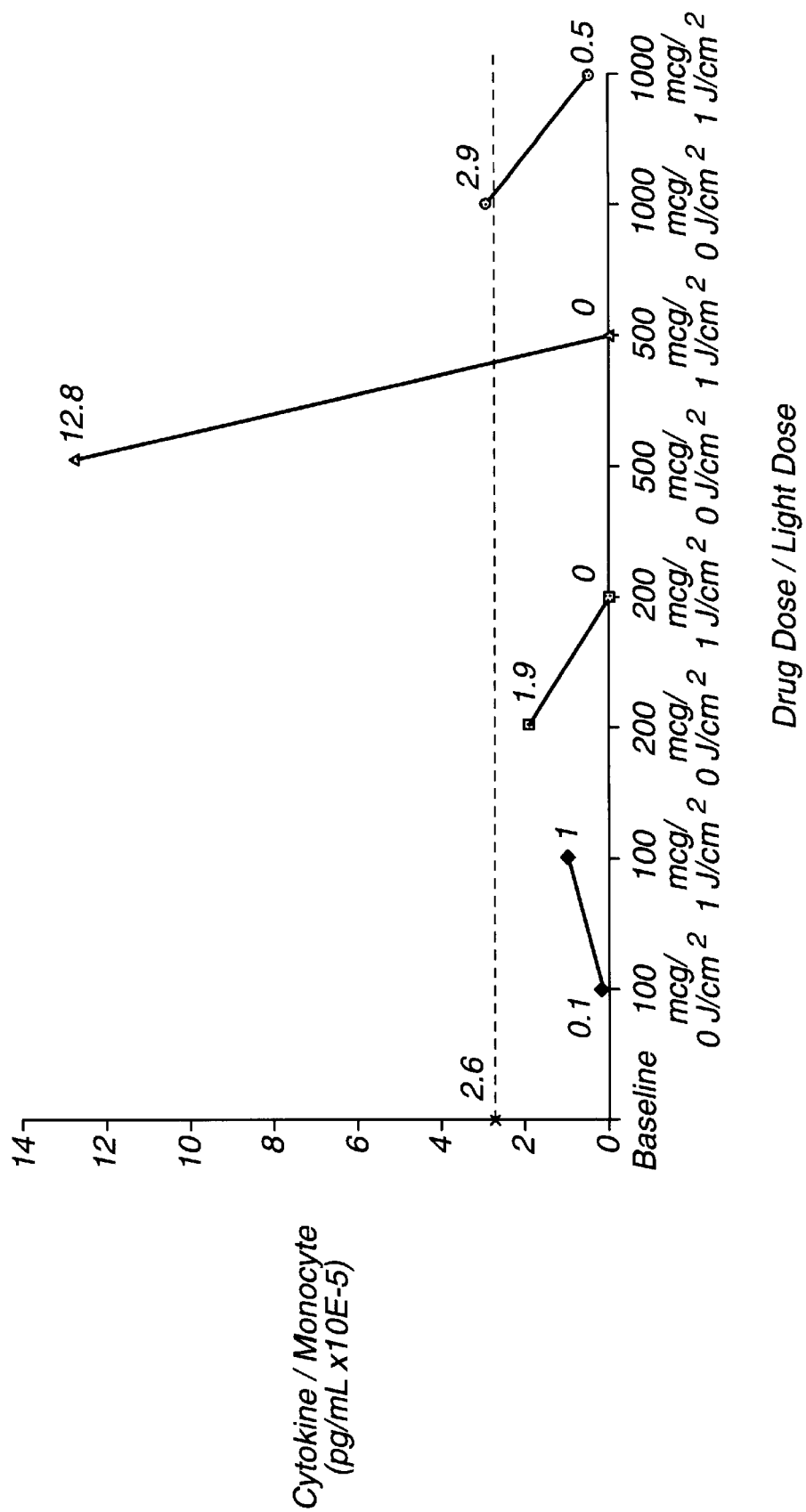

PHOTOPHERESIS TREATMENT OF LEUKOCYTES

This application claims benefit of U.S. Provisional Application Ser. No. 60/014,269 filing date Mar. 29, 1996 pending application Ser. No. 60/029,893 filing date Nov. 8, 1996 pending.

BACKGROUND OF THE INVENTION

Extracorporeal photopheresis is a process where 8-Methoxypsoralen (8-MOP), a naturally occurring light-sensitive compound, is administered orally two hours prior to treatment; blood is then withdrawn from the patient, anticoagulated, and the white blood cells are separated by centrifugation and collected as a leukocyte enriched fraction. These 8-MOP containing leukocytes are then irradiated with ultraviolet A light (UVA) which binds the 8-MOP to pyrimidine bases in DNA and to intra- and extra-cellular proteins. These treated leukocytes are returned to the patient, and the result is an immunomodulation which has been found to be of clinical benefit in a number of disease states[1].

There are a number of diseases which are felt to primarily involve T-cells or are T-cell mediated. Diseases such as cutaneous T-cell lymphoma, organ allograft rejection after transplantation, progressive systemic sclerosis (PSS), inflammatory bowel disease (IBD), rheumatoid arthritis (RA) and juvenile onset diabetes mellitus (JODM) are thought to be T-cell mediated.

Cutaneous T-cell lymphoma (CTCL) is a malignant disease that is progressive. Therapeutic options are limited. Edelson et al. performed a multi-center trial[2] which showed that 24 of 29 (83%) of erythrodermic patients experienced a significant improvement in their disease. These positive responses were seen at a median time of 22.4 weeks after initiation of therapy. Of clinical significance, these patients were those whose diseases were resistant to prior therapy which is felt to be a poor prognostic group. In addition, a decrease in the amount of peripheral blood involvement (Sezary cells) was seen. Actuarial data had indicated that median survival was increased to greater than 60 months from the onset of treatment in comparison with a historical median survival time of less than 30 months. In this original group of patients, remissions were sustained in eight of the subjects who were leukemic. Adverse reactions associated with photopheresis were rare.

Autoimmune diseases are characterized by a dysregulation of the immune system, characterized by specific cellular or humoral mediated destruction of specific organs or tissues in the patient. Examples of such diseases are rheumatoid arthritis and progressive systemic sclerosis.

Rheumatoid arthritis (R.A.) is an inflammatory disease that ultimately leads to joint destruction and is a generalized disease involving many organ systems. There are many pharmaceutical agents in use for R.A., however well tolerated agents with disease modifying potential are needed in as much as the disease is lifelong. In particular, a loss of efficacy and disease progression is seen in a high number of patients after starting secondary line therapy for R.A. Many of the second line agents are immunosuppressive and are themselves the reason for the major side effects such as infection. The need for development of a more specific, non-toxic immunomodulating therapy[3] is great.

Progressive systemic sclerosis (PSS) is a connective tissue disease characterized by inflammatory and fibrotic changes in the skin and viscera. Treatment has been difficult. Anti-inflammatory drugs and corticosteroids are helpful in the early stages of the disease, but do not appear to influence the progression of the disease. Trials with D-penicillamine, methotrexate, cyclosporine, calcium channel blockers and prostagladins are underway, but these agents do not appear to influence the overall progression of the disease. As this disease has been considered to be T-cell mediated, Rock and colleagues have treated PSS patients with photopheresis[4]. In this trial, 56 patients were enrolled into a randomized non-blinded clinical trial. A significantly higher response rate was seen in the photopheresis treated group (68% response rate) compared to the D-penicillamine (control) group (32% response rate).

Juvenile onset diabetes mellitus (JODM) is felt to be mediated by the immune system resulting in the destruction of the cells in the pancreas responsible for the production of insulin. Patients with this disorder have not only dysregulation of their blood sugar levels, but the disease is characterized by a vasculopathy, resulting in specific organ damage leading to significant morbidity and mortality.

IBD is either limited to the colon (ulcerative colitis) or affects both the colon and the small intestine. In addition, there are intraintestinal manifestations of the disease including pyoderma gangrenosum, erythema nodosum, sclerosing cholangitis, ankylosing spondylitis, hepatitis, arthritis, uveitis. IBD involves a dysfunction of the immunoregulatory mechanisms that downregulate immune responses to digestion products, while maintaining the ability to develop a specific immune response to pathogens. Exposure to methoxsalen, activated by UV light, modulates immunoregulatory function, allowing the mucosal T-cenls to mount a lower proliferative response to common microbial antigens than periferal T-cells.

Other T-cell mediated phenomena include rejection of tissues that are foreign to the host. In the case of organ allograft transplantation, it is desirable to prevent this rejection with respect to the transplanted organ, however to otherwise maintain the competence of the immune system, in order to allow the body to combat infection and to allow other normal body defenses. The standard treatments after transplantation are limited as the immunosuppression regimens used to cause a state of general immunosuppression, which leads to the most common adverse reaction to this treatment, again infection, which may be microbial or opportunistic infection. Immunomodulation which does not have broad immunosuppressive properties would be more desirable. Photopheresis has been shown to be effective, and investigators at Loyola University have been able to successfully treat with photopheresis 13 of 14 cases of cardiac rejection refractory to standard immnunosuppressive agents. In a variation of this situation, photopheresis has been successfully used to treat a patient with chronic graft versus host disease[5]. This disorder is characterized by an introgenically induced immunoincompetent host, where immune competent cells (bone marrow or peripheral stem cells) are infused into a patient in such situations as treatment for various malignancies and leukemia. Here the transplanted immunocompetent cells attack the patient (the "host"), and the issue is to modulate the immunocompetent cells without causing further broad immunosuppression and the side effects thereof.

Photopheresis involves the extracorporeal exposure of peripheral blood leukocytes to 8-methoxypsoralen (8-MOP) photoactivated by ultraviolet A light, followed by the reinfusion of the treated white blood cells.

8-methoxypsoralen molecules in the blood enter the white blood cell nuclei and intercalate in the double-strand DNA helix. In an extracorporeal circuit, long wave ultraviolet light is directed at the leukocyte-enriched blood fraction within the UVAR® Photopheresis System. The photoactivated drug, responding to the UVA energy, links to the thymidine base in the DNA helix. This results in cross-linking of thymidine bases which prevents the unwinding of the DNA during transcription. The plasma and altered leukocytes are then reinfused into the patient. The reinfusion of the photopheresis damaged leukocytes results in an delayed immune attack against these damaged leukocytes, as well as, otherwise unmodified WBC's displaying the same cell surface antigens.

Methoxsalen is a naturally occurring photoactive substance found in the seed of the Ammi majus (umbelliferae plant). It belongs to a class of compounds known as psoralens or furocoumarins. The chemical name is 9-methoxy-7H-furo[3,2-g][1]-benzopyran-7-one. The formulation of the drug is a sterile liquid at a concentration of 20 mcg/mL in a 10 mL vial. The pharmacokinetic activity of methoxsalen is available in the investigator's brochure[6]. Toxicology studies of extracorporeal photochemotherapy and different dosages of UVADEX® and ultraviolet light in beagle dogs is lo located in the investigator's brochure.

UVAR System

The treatment consists of three phases including: 1) the collection of a buffy-coat fraction (leukocyte-enriched), 2) irradiation of the collected buffy coat fraction, and 3) reinfusion of the treated white blood cells. The collection phase has six cycles of blood withdrawal, centrifugation, and reinfusion steps. During each cycle, whole blood is centrifuged and separated in a pediatric pheresis bowl. From this separation, plasma (volume in each cycle is determined by the UVAR® Instrument operator) and 40 ml buffy coat are saved in each collection cycle. The red cells and all additional plasma are reinfused to the patient before beginning the next collection cycle. Finally, a total of 240 ml of buffy coat and 300 ml of plasma are separated and saved for UVA irradiation.

The irradiation of the leukocyte-enriched blood within the irradiation circuit begins during the buffy coat collection of the first collection cycle. The collected plasma and buffy coat are mixed with 200 ml of heparinized normal saline and 200 mg of UVADEX® (water soluble 8-methoxypsoralin). This mixture flows in a 1.4 mm thick layer through the PHOTOCEPTOR® Photoactivation Chamber, which is inserted between two banks of UVA lamps of the PHOTOSETTE®. PHOTOSETTE® UVA lamps irradiate both sides of this UVA-transparent PHOTOCEPTOR® chamber, permitting a 180-minute exposure to ultraviolet A light, yielding an average exposure per lymphocyte of 1-2 $J/cm^2$. The final buffy coat preparation contains an estimated 20% to 25% of the total peripheral blood mononuclear cell component and has a hematocrit from 2.5% to 7%. Following the photoactivation period, the volume is reinfused to the patient over a 30 to 45 minute period.

Systems employing these techniques are known whereby extracorporeal treatment of a patient's blood is undertaken. For example, in U.S. Pat. No. 4,573,960—Goss, a patient is given a drug that requires photoactivation and the patient's blood is then withdrawn and separated into its components. The untreated components (red blood cells, some plasma, etc.) are returned to the patient. The patient is then disconnected from the treatment apparatus and the separated components, e.g., white blood cells, are exposed to ultraviolet light. Following photoactivation, the treated cells are returned to the patient.

In U.S. Pat. Nos. 4,321,919; 4,398,906; and 4,464,166, issued to Edelson, the external treatment methods for diseases in which there is a pathological increase of lymphocytes, such as cutaneous T-cell lymphoma, have been discussed. In these methods the patient's blood in the presence of a chemical or an antibody is irradiated with ultraviolet light. Ultraviolet light effects a bonding between the lymphocytes and the chemical or antibody thus inhibiting the metabolic processes of the lymphocytes.

A variety of human viruses are able to infect and replicate within mononuclear cells, or infectious viral particles may remain present within the mononuclear cells. The mononuclear cells can act as either a source for viral replication and spread of the virus, or as a reservoir of infectious virus particles which is difficult for the immune system to eliminate. Failure to eliminate these sources of infectious virus may lead to the establishment of a chronic condition. Viruses which can infect, replicate within, or reside in mononuclear cells include, but are not limited to, arthropod borne viruses, enteroviruses, paramyxoviruses (RSV), herpes viruses, cytomegalo-virus (CMV), Epstein-Barr virus (EBV), hepatitis B virus (HBV), hepatitis C virus (HCV), hepatitis D virus (HDV), hepatitis G virus (HGV), and retroviruses (such as HIV).

A variety of human non-viral pathogenic agents are able to infect and replicate within mononuclear cells, or the infectious non-viral pathogenic agents may remain present within the mononuclear cells. The mononuclear cells can act as either a source for replication and spread of the non-viral pathogenic agents, or as a reservoir of infectious non-viral pathogenic agents which is difficult for the immune system to eliminate. Failure to eliminate these sources of infectious non-viral pathogenic agents may lead to the establishment of a chronic condition. Non-viral pathogenic agents which can infect, replicate within, or reside in mononuclear cells include, but are not limited to, bacteria such as arthropod-borne bacteria, mycoplasma species, and mycobacteria species, and parasites such as plasmodium species and other arthropod-borne parasites.

Extracorporeal photopheresis (ECP) has been successfully used to treat HIV infection (U.S. Pat. No. 4,960,408) and psoralen compounds with long wavelength ultraviolet light have been shown to inactivate certain viruses in vitro, such as HIV (Quinnan, G. V. et al., 1986, Transfusion, 26, pp 481; Bisaccia, A. et al., 1990, Am. Intern. Med., 113, pp 270; Bisaccia, A. et al., 1991, Ann. NY Acad. Sci., 636, pp 321), and influenza virus and herpes simplex virus (Redfield, D. C. et al., 1981; Infect. and Immun., 32, pp 1216). Bisaccia from Columbia University has studied ECP in a pilot trial as therapy for patients with AIDS-related complex. The rationale was that a combination of psoralen with UVA activation could damage HIV in vitro and that reinfusion of the damaged virus may initiate an immune response. The authors found that ECP produced an increase in the HIV-Ab production, increase in the CD8(+) lymphocytes, a decrease in the p24 antigen titer and the inability to culture HIV in 3 patients. Eleven of the 20 patients had improvement in their skin test antigen reactivities.

In addition, a reduced incidence of infection episodes was reported in patients receiving photopheresis treatment for immunosuppression following transplant surgery (Meiser, B. M. et al., 1994, Transplantation, 57, pp. 563). However, the results observed for the transplant surgery patients did not correlate with photopheresis treatment since infection episodes in general were recorded including patients who received a variety of treatments to prevent rejection of the transplanted organ.

Hepatitis C is a common and major cause of serious liver disease and cirrhosis. Approximately 200 million people in the world are currently estimated to be infected with the hepatitis C virus. The prevalence in the United States is estimated to be 0.6 to 1.0% of the population or approximately 3.5 million people[7]. It is reported that chronic hepatitis develops in at least half of those patients with acute hepatitis C. 20% of those will develop liver cirrhosis[8,9].

The HCV genome is a small, enveloped, single stranded, positive-sense RNA virus[10]. It resembles viruses in the Flaviviridae family, both the flaviviruses (dengue and yellow fever viruses) and the pestiviruses[11]. The HCV genome contains one large open reading frame encoding approximately 3000 amino acids[12].

The 5' end starts with a non-coding region. The next structures are the C region which encodes the core of the virus, E1 and E2 are the envelope glycoproteins of the virus. The E2/NS 1 region contain a hypervariable region. Mutations within this area appear to change outer envelope epitopes resulting in escape from immune recognition. Regions NS2 through NS5 all encode nonstructural proteins necessary for viral replication.

The RNA-dependent RNA polymerase has no proofreading ability. This results in a high error rate during replication causing genomic variants to form. A consensus system for genotype classification of the hepatitis C virus has recently been developed. This classification system acknowledges at least six major genotypes of hepatitis C (genotypes 1–6) present worldwide[13]. Each major genotype is further subdivided into 0–3 minor genotypes designated a, b and c. Genotypes 1a (35%) and 1b (35%) are the most common genotypes in the United States. In Western Europe, types 1, 2 and 3 are common. Type 4 is mainly found in Africa and type 5 is associated with Dutch ancestry and is present in South A-frica and the Netherlands. Type 6 is prevalent in Hong Kong. Infection by HCV variants have different rates of progression to cirrhosis, sensitivity to interferon and possibly, to rate of development to hepatocellular carcinoma.

The application of the PCR technique to amplify reverse-transcribed DNA provides a very sensitive assay for detection viral RNA. PCR assays have been able to detect HCV RNA within only a few days of exposure to the virus, weeks before elevations of viral antibody levels[14,15]. This assay can be used to directly monitor the antiviral effect of therapy[16].

The fundamental defect that allows establishment of chronic hepatitis C following acute HCV infection is not known. Several investigators have suggested that impaired cellular immunity, either T cells or natural killer cells, may play a role. Weiner et al. have demonstrated the existence of a hypervariable region of the HCV genome in the E2/NS 1 segment[17]. This area codes for isolate-specific, B-cell antibody binding linear epitopes that are expressed on the envelope surface of the HCV particle. The characteristics of this domain are similar to the V3 loop of HIV-1's gp 120 protein. The rapid mutation within this region may explain a loss of immune recognition and clearance of the hepatitis C virus.

The basic immune mechanism which results in the clearance of hepatitis C virus is still not known. Shirai from the National Cancer Institute has demonstrated that CD8(+) cytotoxic lymphocytes recognize a nonstructural protein with homology to RNA polymerase expressed in association with an HLA class I antigen on the surface of the hepatocytes[18]. The hepatitis C virus is a positive strand virus that replicates by producing a negative-strand RNA as a template. During active HCV replication, these negative-strand RNA templates are present in the patient's liver. Investigators have also found the presence of active, replicating hepatitis C viral particles in the patient's peripheral blood mononuclear cells[19]. Monocytes, macrophages, T-cells and B-cells can all be shown to contain negative-strand HCV RNA.

Subtle changes in monocyte function have been observed in patients chronically infected with HCV as compared to matched controls. In this study by Mendoza and others, [20]PBMC and purified monocytes from HCV-seropositive patients and uninfected controls were stimulated with PMA. Supernatants from the chronic HCV carriers secreted less IL1 and TNF compared to matched uninfected controls. These findings suggest that functional impairment of macrophages may exist during chronic HCV infection and may be the mechanism by which HCV infection persists.

During therapy with alpha interferon, hepatitis C virus can disappear from the patient's liver and blood as measured by RT-PCR. Despite this apparent clearance of virus, there is a very high (80–20 85%) relapse rate after interferon therapy. Investigators have demonstrated the (few) patients who do not have HCV replication detected in the PBMCs at the end of therapy, do not relapse after interferon therapy and are apparent cures[21,22,23].

It would appear that the mononuclear cell can serve as an immunologically protected site that shelters the hepatitis C virus from immune system recognition and attack. Once therapy with alpha interferon is withdrawn, the virus may leave the PBMCs and reinfect the patient's blood and liver.

SUMMARY OF THE INVENTION

The present invention is drawn to a method of treating infections of mononuclear blood cells, including viral infections other than HIV, bacterial infections, and parasitic infections, using extracorporeal photopheresis. In particular, patients with acute and chronic or occult infections which involve mononuclear cells are treated by the method of the present invention and the level or presence of infectious agent genetic material is reduced or undetectable in patients so treated. The present invention is also drawn to a method of treating chronic viral infections, other than HV, involving mononuclear cells within which certain viruses replicate or in which infectious viral particles reside. The present invention is also drawn to the alteration or modulation of monocyte function through the use of the method of photopheresis. The method of the present invention involves the treatment of a patient's blood with a photoactivatable or photosensitive compound which is capable of binding to nucleic acids in infected nucleated cells upon activation of the compound by ultraviolet light. The photoactivatable or photosensitive compound may be administered to the patient's blood in vitro or in vivo by conventional administration techniques.

A portion of the patient's blood is then treated extracorporeally using photopheresis, which comprises subjecting the blood to ultraviolet light, preferably long wavelength ultraviolet light in the wavelength range of 320 nm to 400 nm, commonly called UVA light. The treated blood, or a fraction thereof, is returned to the patient following extracorpoiral photopheresis to modulate monocyte function and/or stimulate an immunological response by the patient's immune system against the infected cell population and/or against the virus to inhibit progression of the viral infection. The viral genetic material is also damaged by this treatment, rendering the virus incapable of replication, thereby interrupting the spread of the virus and neutralizing infectious viral particles that reside in the cells. The cellular genetic material is also damaged by this treatment which may result in the alteration or modulation of monocyte function as disclosed herein.

BRIEF DESCRIPTION OF THE DRAWINGS

FIG. 1, Panel A, Panel B, and Panel C show the modulation of monocyte function by measuring levels of NF-α, IL-1β, and IL-6, respectively, following treatment with drug only, without light treatment.

FIG. 2, Panel A, Panel B, and Panel C show the modulation of monocyte function by measuring levels of TNF-α, IL-1β, and IL-6, respectively, following treatment with drug and with light treatment.

DETAILED DESCRIPTION OF THE INVENTION

The present invention is directed to the use of photopheresis to inactivate or interrupt the replication cycle of pathogenic agents such as bacteria, parasites and viruses, and/or modify or kill blood cells which have been infected with such agents. While it is not intended that the scope of the present invention be limited by any specific theory of operation, it is believed that infections which are not controlled by the normal immunological response of a patient can be treated by damaging infected nucleated blood cells (such as mononuclear cells) using a photopheresis treatment according to the invention. The treated cells as well as killed and/or attenuated virus, peptides, native subunits of the virus itself (which are released upon cell break-up and/or shed into the blood) and/or pathogenic noninfectious viruses are then used to generate an immune response.

It is readily apparent to those skilled in the art that the method of the present invention is useful against a wide variety of human pathogenic agents including but not limited to those bacteria, parasites and viruses which infect, replicate in, or reside as infectious agents in, mononuclear blood cells.

A variety of human viruses are able to infect and replicate within mononuclear cells, or infectious viral particles may remain present within the mononuclear cells. The mononuclear cells can act as either a source for viral replication and spread of the virus, or as a reservoir of infectious virus particles which is difficult for the immune system to eliminate. Failure to eliminate these sources of infectious virus may lead to the establishment of a chronic condition. Viruses which can infect, replicate within, or reside in mononuclear cells include, but are not limited to, arthropod borne viruses, enteroviruses, paramyxoviruses (RSV), herpesviruses, cytomegalovirus (CMV), Epstein-Barr virus (EBV), hepatitis B virus HBV), hepatitis C virus (HCV), hepatitis D virus (HDV), hepatitis G virus (HGV), and retroviruses (such as HIV). While the treatment methods according to the present invention can be applied to the treatment of any virus infection, they are particularly useful in the treatment of CMV and HCV infection.

Ideal therapy, for the patient who has, for example, a hepatitis C virus infection, would clear virus from the liver, blood and infected mononuclear cells simultaneously. Extracorporeal photochemotherapy using methoxsalen (photopheresis) is believed to cause an immunization against the abnormal (cancerous, in the case of CTCL) T-cells. During photopheresis, methoxsalen enters the white blood cell nuclei and intercalates in the double-strand DNA helix. In an extracorporeal circuit, long wave ultraviolet light is directed at the leukocyte-enriched blood volume. The methoxsalen, responding to the UVA energy, links to the thymidine base in the DNA helix. This results in the cross-linking of thymidine bases which prevent the unwinding of the DNA during transcription. Ultraviolet A light (UVA) damages abnormal T-cells rendering them more immunogenic. After cells are photoactivated, reinfusion of these altered T-cells causes an immunological reaction that targets T-cells carrying the same surface antigens[24]. This results in the production of a highly specific immune response against the abnormal cells (either a cancer clone or perhaps T-cells which express viral antigens on their surface). It is estimated that approximately 25–50% of the total peripheral blood mononuclear cell 5 compartment is treated per photopheresis session (2 consecutive days schedule).

Work by Vowels[25] demonstrated monocytes treated in an extracorporeal circuit of plasma containing 8-methoxypsoralen and exposure to ultraviolet-A light (photopheresis) releases tumor necrosis factor-alpha, IL-1, IL-6, and possibly IL-8. It is believed that photopheresis modulates the activity of peripheral blood monocytes/macrophages.

In addition, ideal therapy should not be affected by the hepatitis C's hypervariable E2/NS I region tendency to mutate. Changes in the viral particle envelope antigens may cause an escape from the B-cell HCV-neutralizing antibodies (escape mutants). Extracorporeal photochemotherapy using methoxsalen may induce damage to any free viral particles in the irradiated blood. This therapy could also induce an immune response to any newly formed hepatitis C escape mutants.

A variety of human non-viral pathogenic agents are able to infect and replicate within mononuclear cells, or the infectious non-viral pathogenic agents may remain present within the mononuclear cells. The mononuclear cells can act as either a source for replication and spread of the non-viral pathogenic agents, or as a reservoir of infectious non-viral pathogenic agents which is difficult for the immune system to eliminate. Failure to eliminate these sources of infectious non-viral pathogenic agents may lead to the establishment of a chronic condition. Non-viral pathogenic agents which can infect, replicate within, or reside in mononuclear cells include, but are not limited to, fungi, bacteria such as arthropod-borne bacteria, mycoplasma species and mycobacteria species, and parasites such as plasmodium species and other insect-borne parasites. It is readily apparent to those skilled in the art that the method of the present invention is useful for the treatment of infections of mononuclear blood cells by the agents described above.

According to the claimed methods, a photoactivatable or photosensitive compound is first administered to the blood of a patient who is infected with a virus of a type which attacks nucleated blood cells. The photoactivatable or photosensitive compound may be administered in vivo (e.g. orally or intravenously) or may be administered in vitro to a portion of the patient's blood which has been removed from the patient by employing conventional blood withdrawal techniques.

In accordance with the present invention, the photoactivatable or photosensitive compound should be capable of binding to nucleic acids upon activation by exposure to electromagnetic radiation of a prescribed spectrum, e.g., ultraviolet light.

Next, the portion of the patient's blood to which the photoactive compound has been administered is treated by subjecting the portion of the blood to photopheresis using ultraviolet light. The photopheresis step is preferably carried out in vitro using an extracorporeal photopheresis apparatus. The photopheresis step in accordance with the present invention may also be carried out in vivo. A presently preferred extracorporeal photopheresis apparatus for use in the methods according to the invention is currently manufactured by Therakos, Inc., under the name UVAR®. A description of such an apparatus may be found in U.S. Pat. No. 4,683,889. The exposure of blood to ultraviolet light in a photopheresis apparatus is within the ability of persons having ordinary skill in the art.

When the photopheresis step is carried out in vitro, at least a fraction of the treated blood is returned to the patient to increase the patient's immune response to the infected cell population and to the virus itself Preferably, the treatment method described herein is repeated at an interval of about once per week to about once every four weeks. Preferred photoactive compounds for use in accordance with the present invention are compounds known as psoralens (or furocoumarins) which are described in U.S. Pat. No. 4,321,919. Alternatively, the patient's blood can be separated on a standard photopheresis-type device and photoactivated on a separate device.

The preferred photoactivatable or photosensitive compounds for use in accordance with the present invention include, but are not limited to, the following: psoralen; 8-methoxypsoralen; 4,5',8-trimethylpsoralen; 5-methoxypsoralen; 4-methylpsoralen; 4,4-dimethylpsoralen; 4-5'-dimethylpsoralen; 4'-aminomethyl-4,5',8-trimethylpsoralen; 4'-hydroxymethyl-4,5',8-trimethylpsoralen; and 4',8-methoxypsoralen. The most particularly preferred photosensitive compound for use in accordance with the invention is 8-methoxypsoralen.

The photosensitive compound, when administered to the patient's blood in vivo is preferably administered orally, but also can be administered intravenously and/or by other conventional administration routes. The preferred oral dosage of the photosensitive compound is in the range of about 0.3 to about 0.7 mg/kg. most preferably about 0.6 mg/kg.

When administered orally, the photosensitive compound should preferably be administered at least about one hour prior to the photopheresis treatment and no more than about three hours prior to the photopheresis treatment. If administered intravenously, the times would be shorter.

Alternatively the photosensitive compound may be administered to the patient's blood following its withdrawal from the patient, and prior to or contemporaneously with exposure to ultraviolet light. The photosensitive compound may be administered to whole blood or a fraction thereof provided that the target blood cells or blood components receive the photosensitive compound.

The photopheresis treatment in the treatment methods according to the present invention is preferably carried out using long wavelength ultraviolet light (UVA) at a wavelength within the range of 320 to 400 nm. The exposure to ultraviolet light during the photopheresis treatment preferably has a duration of sufficient length to deliver about 1-2 $J/cm^2$ to the blood.

When the photopheresis treatment according to the present invention is carried out in vivo, careful attention should be paid to controlling the maximum radiant exposure so as to avoid unnecessary injury to the patient. Methods for calculating maximum radiant exposure to ultraviolet light are known in the art.

The invention also provides methods for making vaccines against the infectious agent or pathogen. According to the present invention, a donor who is infected with, for example, a virus, such as CMV or HCV may be utilized to produce a vaccine against his virus infection as follows.

First, a photosensitive compound as described hereinabove is administered to at least a portion of the donor's blood either prior to removal of the blood, either orally or intravenously, or after removal from the patient in which case it is administered in vitro. Optionally, a portion of the donor's blood could first be processed using known methods to substantially remove the erhythrocytes and the photoactive compound is then administered to the resulting enriched leukocyte fraction.

In any case, the portion of blood (or enriched leukocyte fraction thereof) to which the photosensitive compound has been administered is subjected to a photoactivation treatment using ultraviolet light, preferably UVA in the manner previously described. The treated blood or the treated enriched leukocyte fraction (as the case may be) is then administered back to the donor.

The following Examples are provided to illustrate the present invention and are not to be construed as a limltation thereon.

EXAMPLE 1
Reduction of CMV in Transplant Patients

Patients randomized to the clinical centers in the United States had repeated samples drawn for CMV DNA analysis using PCR. Since this method was considered to be highly sensitive, it was thought that the positive predictive value, i.e., prior to a patient developing a CMV infection, may have utility for a treating physician. It was recognized prior to the start of the trial that this hypothesis could only be tested if patients developed a CMV infection during the 180 day treatment period, however, the duration of time a patient tested negative for the virus would also be considered an important finding. This Example focuses on the latter of the two endpoints, given that only 11 of the 61 (18.0%) randomized patients developed clinical CMV which required treatment.

Samples obtained from patients participating in the cardiac transplant trial were analyzed for CMV DNA using PCR. The individuals who were performing the tests were blinded to all information regarding treatment assignment and time on study. Two 1-microliter samples were drawn from each specimen. The sensitivity of the procedure was considered to be 6000 replicate copies of the DNA virus. If greater than 6000 copies were detected, the sample was given a positive rating. The false negative rate for this procedure was predetermined to be 2/30 (6.7%), suggesting that the 6000 copy cutoff was valid in determining if the virus was present.

The CMV status of the donor and recipient were used to classify patients according to their risk for developing a CMV infection. Nineteen of the 28 patients were grouped as "high" risk by receiving an organ from a positive CMV donor. Ten of the 19 recipients were also positive prior to transplantation, while the remaining 9 patients tested negative. All transplanted patients received varying prophylaxis treatment for CMV depending upon the risk category to which they were assigned. Twelve of the 19 high risk patients (63.2%) were randomized to receive photopheresis with standard immunosuppression therapy, the remaining 7 (36.8%) high risk patients received only standard immunosuppression therapy. Low risk patients were negative for the virus prior to transplantation and had a CMV-negative donor. Of the 4 low risk patients, 3 were randomized to receive standard immunosuppression therapy, the remaining patient received photopheresis with standard immunosuppression therapy. Although not significant (2-tailed Fisher's Exact test p=0.281), a greater proportion of patients randomized to receive photopheresis with standard immunosuppression therapy were classified in the high risk group, and a lower proportion existed in the low risk group. Assuming photopheresis had no effect on the viral burden, a greater proportion of the patients in the photopheresis arm would be expected to have a greater proportion of positive 30-day intervals as a result of their relative risk classification.

Repeated samples for CMV analysis were obtained over a 180 day period following transplantation from 28 patients randomized to receive either photopheresis with standard immunosuppression (n=17) or standard immunosuppression alone (n=11). Since a disproportionate number of specimens were obtained for each patient (range 2–19), the last CMV reading from consecutive 30 days intervals from date of transplant was used in the analysis. This method normalized the data, allowing a valid comparison to be made between the two treatment groups. Given the frequency that samples were obtained for CMV analysis, 30 day intervals from the date of transplant provided a reasonable intra-patient profile from which to assess response. No CMV samples were available for 31 of the 168 30-day intervals (18.5%), suggesting that tightening the duration of the interval would only contribute to the pattern of missingness. There was no significant difference (2-tailed Fisher's Exact test p=0.421) between the proportion of intervals without CMV values between the treatment groups (photopheresis with standard immunosuppression; 21/102 v. standard immunosuppression: 10/66). Given the sensitivity of the test, if either replicate revealed the sample was positive for the virus, the sample was viewed as being positive. Therefore, the only samples considered to be negative in the analysis were those that were negative in repeated tests.

The number of 30-day intervals a patient tested negative for the virus was reduced to a proportion and adjusted for using the number of intervals in which a CMV determination had been made. A rank order examination (Kruskal-Wallis test) revealed a significant difference (p=0.036) in favor of the patients randomized to receive photopheresis with standard immunosuppression therapy. Results of this analysis indicate that photopheresis, in conjunction with standard immunosuppression therapy, reduces CMV to a level that was undetected, as shown in Table 1.

TABLE 1

Reduction in the level of CMV DNA

| Intra-Patient Percentage of CMV Positive Tests | Percentage of patients with CMV infection-free tests | | | |
|---|---|---|---|---|
| | By Category | | Cumulative | |
| | Photopheresis Treated | Standard Treatment | Photopheresis Treated | Standard Treatment |
| 0–20% | 29.4 | 18.2 | 18.2 | 18.2 |
| 21–40% | 47.1 | 9.1 | 76.5 | 27.3 |
| 41–60% | 11.8 | 18.2 | 88.3 | 45.5 |
| 61–80% | 5.9 | 45.4 | 94.2 | 90.9 |
| 81–100% | 5.9 | 9.1 | 100 | 100 |

Patients treated with photopheresis and standard triple drug therapy had significantly fewer positive tests than patients treated with standard triple drug therapy alone (Table 1). Seventy six percent of the photopheresis patients had 40% or fewer positive tests, assessed on an intra-patient basis. The equivalent proportion of patients randomized to standard triple drug therapy had over 60% positive tests.

EXAMPLE 2

Treatment of Chronic Viral Infections of Mononuclear Blood Cells

A patient diagnosed as having a chronic viral infection of the mononucleated blood cells is administered a photoactivatable compound, either systemically or by oral administration, or ex-vivo administration into the leukocyte enriched blood fraction. After standard veinous access is established, a portion of the patient's blood is anticoagulated either through systemic bolus administration with minimal administration to the extracorporeal circuit, or ex-vivo administration alone. A portion of the patient's blood is removed, preferably pumped into the extracorporeal circuit, and centrifuged to separate the whole blood fractions distinguished by cell mass, typically plasma, buffy coat (leukocyte enriched fraction) and red blood cells. A portion of the plasma and buffy coat remains in the extracorporeal circuit, and all red blood cells are returned to the patient. The saved portion of the plasma and buffy coat are exposed to ultraviolet light for a sufficient time to photoactivate the photosensitive compound with about 1-2 J/cm. After photoactivation is complete the patient is reinfused with the treated leukocyte enriched blood fraction over a period of about 30 to 60 minutes.

This process is repeated typically on two consecutive days every one to two weeks for a period of time of typically not less than six months. Treatment is continued at a frequency that is deemed necessary in order to maintain the therapeutic effect.

EXAMPLE 3

Treatment of Acute Viral Infections of Mononuclear Blood Cells

A patient diagnosed as having an acute viral infection of the mononucleated blood cells is administered a photoactivatable compound, either systemically or by oral administration, or ex-vivo administration into the leukocyte enriched blood fraction. After standard veinous access is established, a portion of the patient's blood is anticoagulated either through systemic bolus administration with minimal administration to the extracorporeal circuit, or ex-vivo administration alone. A portion of the patient's blood is removed, preferably pumped into the extracorporeal circuit, and centrifuged to separate the whole blood fractions distinguished by cell mass, typically plasma, buffy coat (leukocyte enriched fraction) and red blood cells. A portion of the plasma and buffy coat remains in the extracorporeal circuit, and all red blood cells are returned to the patient. The saved portion of the plasma and buffy coat are exposed to ultraviolet light for a sufficient time to photoactivate the photosensitive compound with about 1-2 J/cm. After photoactivation is complete the patient is reinfused with the treated leukocyte enriched blood fraction over a period of about 30 to 60 minutes.

This process is repeated typically on two consecutive days every one to two weeks for a period of time typically not less than three months. Treatment is continued at a frequency that is deemed necessary in order to maintain the therapeutic effect and eliminate the acute infection.

EXAMPLE 4

In-vitro Comparison of the Effects of Photopheresis Using Multiple Combinations of UVA Light and UVADEX® Doses on Monocyte Function The objective of this study was to assess the effect of different combinations of UVA energy and UVADEX® drug doses on monocyte function in patients with three different HCV viral loads as compared to normal controls.

This protocol consists of two parts. In part 1, 4 subjects will selected for participation based on inclusion/exclusion criteria. One patient was selected at each of the 3 different viral loads; <$10^4$ virus/mL, between a level of $10^4$ and $10^6$ virus/mL, >$10^6$ virus/mL and 1 normal control. All 4 subjects underwent an apheresis donation process which yields 240 mL of buffy coat and 300 mL plasma. This donated fraction was divided into 20 alloquots and were exposed to 4 different light doses and 5 different drug doses. Pretreatment monocyte function was compared to post-treatment samples. HCV load was determined using the PCR method.

Three subjects who have detectable serum HCV RNA by RT-PCR (at three different viral levels) and one healthy control subject were identified. Any subject who was receiving or had received in the last 3 months any anti-viral drug or drug currently approved for, or under investigation for hepatitis C or has a coexisting infection was excluded.

Subjects underwent screening labs to determine eligibility. Once enrolled into the clinical study, the subject had pre-treatment blood tests to assess monocyte function. Immediately after, the subject undergoes an apheresis donation of 240 mL of buffy coat and 300 mL of plasma using the UVAR® Photopheresis Instrument.

Response to different doses of UVA light and UVADEX® was evaluated by an assessment of cell viability by trypan blue exclusion and monocyte function (IL-1, TNF, IL-6 and IL12).

The UVAR® Photopheresis System was currently indicated for the use in "ultraviolet-A irradiation, in the presence of the photoactive drug Methoxsalen (8-methoxypsoralen or 8-MOP) of extracorporeally circulating leukocyte-enriched blood in the palliative treatment of the skin manifestations of Cutaneous T-Cell Lymphoma (CTCL)". This approval was with the oral formulation of the drug methoxsalen and the UVAR® Photopheresis system.

The UVAR® Photopheresis System consists of the UVAR® Instrument, four blood tubing lines, the PHOTO-CEPTOR® Photoactivation Chamber, the PHOTOSETTE-A® Light Assembly and a pediatric 125 mL centrifuge bowl.

The UVAR® Instrument has been carefully engineered to deliver the optimum UVA energy level for effective photoactivation of methoxsalen. A centrifuge for separating the blood fractions during the plasma and buffy coat collection steps was integrated into the UVAR® Instrument with a reversible blood pump, a recirculation pump, an anticoagulation pump, and a system of electromechanical clamps for routing fluid. The UVAR® Instrument also controls blood and recirculation pump speed/direction and also supplies power to the centrifuge. A microprocessor and discrete logic circuits monitor operating parameters throughout treatment and display instrument status and conditions. Microprocessor controls assist the operator in the various stages of the photopheresis procedure.

The Photopheresis Blood Tubing Set was four lines used for collecting, photoactivating and reinfusing the leukocyte-enriched blood. These four lines were the patient/heparin line, the collection/return line, the bowl outlet line and the photoactivation line.

The PHOTOCEPTOR® Photoactivation Chamber was a thin sterile fluid pathway constructed of UVA-transparent acrylic. The PHOTOCEPTOR®'s design allows it to be inserted between the PHOTOSETTE®'s two banks of UVA lamps for photoactivation. The PHOTOCEPTOR®'s fluid pathway loops to form seven channels in which the leukocyte-enriched blood was circulated during photoactivation by UVA light.

The phases of a photopheresis treatment with the UVAR® Photopheresis System include collection of the leukocyte-enriched blood, photoactivation and reinfusion. During a photopheresis treatment, 300 mL of plasma and 240 mL of buffy coat were separated in a pediatric pheresis bowl. From this separation, plasma and buffy coat were saved. Each cycle, plasma volumes were determined by the UVAR® operator and 40 mL were automatically collected after buffy coat was optically selected by the Operator. All red blood cells and additional plasma were reinfused back to the patient before the next collection cycle begins. Liquid methoxsalen (UVADEX®) was injected into the buffy coat bag at the end of cycle #1.

Photoactivation of the leukocyte-enriched blood within the photoactivation circuit begins during cycle #1 of buffy coat collection. Plasma and buffy coat mix with 200 mL of heparinized normal saline (solution used from priming the UVAR instrument). This mixture of plasma, buffy coat and heparinized normal saline was pumped continuously throught the PHOTOCEPTOR® Photoactivation Chamber. The UVA transparent PHOTOCEPTOR® maintains a constant blood film thickness for even penetration of the UVA energy. Photoactivation continues for an additional 1.5 hours after the total volume of 240 mL of buffy coat and 300 mL of plasma was collected. Following photoactivation, this total volume (740 mL total=240 mL buffy coat, 300 mL plasma and 200 mL heparinized normal saline) was reinfused to the patient. Reinfusion was by gravity and recommended reinfusion time was 30 to 45 minutes. In total, the photopheresis procedure takes three to four hours.

In this study, the patient undergoes the apheresis process to remove 240 mL of buffy coat and 300 mL of plasma and was mixed with 200 mL of normal saline from priming the photopheresis instrument. The 740 mL leukocyte enriched blood from the buffy coat bag was divided into 5 equal samples of 148 mL each. Each of these samples was mixed with either 0 ng/mL, or 100 ng/mL (0.74 cc of UVADEX®), or 200 ng/mL (1.48 cc of UVADEX®), or 500 ng/mL (3.7 cc of UVADEX(®), or 1000 ng/mL (7.4 cc of UVADEX®). Each of the five (148 mL) samples were then divided into 4 samples of 37 mL each and was exposed to either 0, 1, 2 or 4 joules of UVA light. After photoactivation was complete, samples were processed for cell viability and monocyte function.

The normal function of the monocyte, as measured by cytokine expression, was modulated by the addition of the UVADEX® drug without treatment with ultraviolet light. As illustrated in FIGS. 1A, 1B, and 1C, the interpatient expression of TNF-α, IL-1β and IL-6, respectively, were different between normals and HCV infected patients.

The combination of UVA light and the photoactivatable drug also modify the function of the monocyte. As seen FIGS. 2A, 2B, and 2C, the intrapatient expression of cytokines TNF-α, IL-1β and IL-6, respectively, was modulated with the addition of UVA light and UVADEX®.

EXAMPLE 5

A Factorial-Designed Pilot Study Using Extracorporeal Photochemotherapy and Alpha Interferon in the Treatment of Patients with Chronic HCV Patients were assigned to one of four treatment arms:

Group 1—ECP weekly (two consecutive day treatments) using 200 mcg of UVADEX for twelve weeks (26 treatments). If there is a response to treatment (i.e. either normalization of serum ALT or clearance of HCV RNA via the PCR assay), patients continued ECP every two weeks for three additional months. If there is no response, ECP is continued weekly and alpha interferon added at a dose of 3 MIU three times weekly. Both therapies are administered for an additional 12 weeks.

Group 2—ECP weekly (two consecutive day treatments) using 200 mcg of UVADEX for twelve weeks (26 treatments) in conjunction with alpha interferon administered at a dose of 3 MIU three times weekly for 12 weeks. If there is a response to treatment (i.e. either normalization of serum ALT or clearance HCV RNA via the PCR assay), patients continued ECP every two weeks and alpha interferon at a dose of 3 MIU three times weekly for a additional 12 weeks. If there is no response, subjects entered the follow-up portion of the protocol.

Group 3—The alpha interferon induction group received alpha interferon alone, administered at a dose of 3 MIU three times a week for 12 weeks. If there is a response to treatment (i.e. either normalization of serum ALT or clearance HCV RNA via the PCR assay), patients continue alpha interferon for 12 additional weeks. If there is no response, alpha interferon is continued at the same dose and ECP using 200 mcg of UVADEX is added with the frequency of administration of treatment being two ECP procedures weekly. Both therapies are administered for 12 weeks.

Group 4—The delayed treatment group are observed for 12 weeks. At the end of the 12 weeks, if there is no ALT normalization or clearance of HCV RNA via the PCR assay, subjects are enrolled into group 2 and followed the group 2 treatment.

Safety and tolerance to treatments using 200 mcg of UVADEX® are assessed when used alone or as part of a combination treatment with alpha interferon.

Adverse events are be assessed as follows:

Compare the frequency and severity of adverse events classified by their relationship to the device, drug and disease among groups 1, 2, and 3.

Compare the frequency of completed photopheresis treatments between groups 1 and 2.

Compare the frequency of abnormal laboratory parameters and new symptomatology at each treatment visit, and monthly during the post-treatment phase for all groups.

Blood is collected to monitior complete blood count, serum chemistry and prothrombin times and new symptomatology is assessed at each visit.

HCV Antibody Immunoassays
ELISA II

ELISA II is a second generation immunoassay which uses the combination c200 antigen. The c200 antigen is a combination of the c22-3 (core region), c33c (NS3) and the c100-3 (NS-4) antigens. This combination provides increased sensitivity and specificity over the first generation assay.

RIBA II

This second generation assay is used to confirm ELISA II positivity. The assay consists of four separate antigen bands (c33c, c22-3, c100-3, 5-1-1) on a plastic strip. Reactivity to two bands confirms ELISA II positivity.

Combination of Extracorporeal Photochemotherapy and Alpha Interferon

The combination of extracorporeal photochemotherapy and alpha interferon has been used in the therapy of patients with advanced forms of cutaneous T-cell lymphoma[44] and in an investigator sponsored study treating cirrhotic patients with chronic hepatitis C who previously failed or relapsed after receiving treatment with interferon alpha. Combination photopheresis plus alpha interferon did not demonstrate any increase in adverse experiences reported than from either therapy used as a single agent.

Primary Efficacy

HCV RNA—Since this research is intended to assess the feasibility and "proof of concept" of photopheresis for treating patients with chronic HCV, intra-patient and group changes from baseline will be taken on face value and used to define the magnitude of response. On an intra-patient basis, a clinically significant decrease in viral load is defined clearance of HCV RNA from pre-treatment baseline values.

For patients that experience clearance of HCV RNA, the time and duration the response is maintained will be calculated on an intra-patient basis and compared among the groups.

Serum ALT—Normalization of serum ALT will be evaluated on an intra-patient basis within the groups and among the groups. In addition, the time to normalization of ALT and the duration the normalization is maintained will be calculated on an intra-patient basis and compared among the groups.

Monocyte Function—Monocytes purified from PBMC collected I hour after the first day of the two day photopheresis session will be evaluated on an intra-patient basis within the groups and among the groups for production of IL-1β, IL6, IL12, and TNF-α as compared to pre-treatment baseline samples.

Study Design

This study is a randomized, 4-arm factorial design, prospective study designed to assess the relative safety and response among balanced groups treated with and without extracorporeal photochemotherapy (photopheresis) and alpha interferon. Patients entering this protocol must have chronic HCV and will meet all inclusion and exclusion criteria. HCV genotype analysis is performed to determine patient eligibility. Once eligibility has been determined, a liver biopsy is performed if it has not been conducted in the past 12 months. All baseline bloodwork is performed including RT-PCR analysis Inclusion Criteria The following criteria must be met to be eligible for randomization:

Age between 18–70

Detectable HCV-RNA by RT-PCR within 4 weeks before randomization. Viral titer must fall between $>1.1\times10^5$ but $<1.0\times10^7$ copies of virus per mL Females of childbearing potential must be HCG negative within 24 hours prior to starting study treatment. Effective birth control must be practiced from one month prior to the study treatments to the end of the treatment phase of the protocol. Females may not be lactating.

Karnofsky performance status of >60 and a life expectancy of at least 12 months

Pre-study laboratory values of:
a) WBC >3.0 cmm
b) Hemoglobin>10.0 mg/dL
c) Platelet count >75,000/UL
d) Total bilirubin <3.0 mg/dL
e) Albumin >2.0 g/dL
f) Prothrombin time not more than 3 seconds beyond normal range
g) Serum creatinine <2.5 mg/dL
h) Mean ALT (2 samples drawn a minimum of one week apart) $\geq 1.2$ times the upper limits of normal Able to provide informed consent Adequate venous access Genotype 1 by Simmonds classification Failed previous therapy with a cummulative dose of at least 3 months treatment with alpha interferon.

Alphafetoprotein (AFP) level must be less than 100 ng/mL. Subjects with AFP >30 but <100 should have a liver ultrasound to rule out hepatocellular carcinoma.

Exclusion Criteria

Patients exhibiting the following criteria will be excluded:

Use of investigational drugs/devices for hepatitis C within the past six months

Exposure to any other antiviral or immuno-suppressant drugs within the past six months. Exposure to IFN up to three months prior to study entry will be allowed.

Major surgery within the past six weeks

Known untreated esophageal varices

History of hepatic failure suggested by:
hepatic encephalopathy
ascites intractable to medical therapy History of chronic liver disease including:
Wilson's disease
Hemochromatosis
Alpha 1 antitrypsin disease
Primary biliary cirrhosis
Drug/alcohol induced liver disease
Autoimmune hepatitis
Primary sclerosing cholangitis
HbsAg or HDV positivity History of recent acute liver disease
Hepatitis A (IgM antibody) positive
Recent mononucleosis
Drug or alcohol induced hepatitis Unable to tolerate the extracorporeal blood volume loss associated with apheresis Photosensitive disease such as porphyria or SLE Hepatotoxic medications within 3 months of enrollment Active, serious, concomitant medical disease (i.e.: cardiac, renal, pulmonary, neurologic, hematologic or dermatologic disease)

Patients with active cancer, psychiatric illness or patients using illicit substances HIV infection as evidenced by anti-HIV positivity Known heparin allergy or idiosyncratic or hypersensitivity to psoralen compounds Previous treatment with alpha interferon with response and then relapse.

Follow-Up Period

All patients are followed after completion of the treatment period to assess for adverse events of delayed onset or persisting from the treatment period. This follow-up period will continue for six months after the last photopheresis and/or until a steady state response (e.g., reduction or loss of detectable HCV) is achieved.

EXAMPLE 6

Modulation of Cytokine Expression in Transplant Patients

Patients were randomized to receive either standard triple drug immunosuppression (Cyclosporine, Imuran and Prednisone) or standard therapy plus photopheresis. Photopheresis treatments were administered 24 times over six months, starting immediately (within 24 hours) post-op. Treatments were always given on two consecutive days. Ten treatments (i.e., five treatment cycles) were administered the first month, four treatments/month for the second and third month, followed by two treatments monthly through month six. Sixty-one patients were randomized at 12 centers worldwide.

All patients were receiving a primary cardiac transplant, were not on any other investigational drug or device and did not receive any antibody therapy (OKT3, ATG or ALG).

All patients were treated with a common, standardized method for steroid taper and treatment of any acute rejection episode. Serial endomyocardial biopsies were taken at a standardized frequency. Patients were followed for six months after the discontinuation of therapy. A significant reduction in the number of patients experiencing multiple rejections was seen in the photopheresis group (Barr, et.al. ASTP/ASTS Joint Plenary Session, 1996 ASTP #342, p. 170). Blood samples were drawn from patients at regular intervals throughout the treatment period. The samples were shipped to a central core laboratory, where soluble interleukins were measured utilizing standard ELISA technology.

TABLE 2

|  | Il-1Beta (U/ml) | IL-6 (ng/ml) | TNF-A (pg/ml) |
| --- | --- | --- | --- |
| Baseline (Day 0 Post-Transplant) | 1.0 | 55.2 | 3.0 |
| Pre-Photopheresis Therapy, Prior to Confirmation of Grade 3A/3B Rejection | 164.4 | 93.4 | 26.7 |
| Post 2-Days of Photopheresis Therapy, Prior to Confirmation of Grade 3A/3B Rejection | 2.3 | 7.9 | 2.8 |

Source: Cardiac Transplant Trial, Patient UCT 1/2

TABLE 3a

Cardiac Transplant USA Trial
IL-1b/Patient 1/2

| Days Post-Treatment | Days on Study | Baseline Value (U/ml) | Post-Treatment Value (U/ml) |
| --- | --- | --- | --- |
| 0 Days | 29 | 1.0 | 8.1 |
|  | 43 | 1.0 | 7.5 |
|  | 57 | 1.0 | 7.7 |
|  | 85 | 1.0 | 2.1 |
| 1 Day | 7 | 1.0 | 2.3 |
|  | 72 | 1.0 | 4.2 |
| 2 Days | 13 | 1.0 | 42.0 |
|  | 20 | 1.0 | 132.1 |
| 3 Days | 5 | 1.0 | 164.4 |

TABLE 3b

Cardiac Transplant USA Trial
TNF-alpha/Patient 1/2

| Days Post-Treatment | Days on Study | Baseline Value (pg/ml) | Post-Treatment Value (pg/ml) |
| --- | --- | --- | --- |
| 0 Days | 29 | 3.0 | 5.7 |
|  | 43 | 3.0 | 3.0 |
|  | 57 | 3.0 | 4.1 |
|  | 85 | 3.0 | 11.6 |
| 1 Day | 7 | 3.0 | 2.8 |
|  | 72 | 3.0 | 13.3 |
| 2 Days | 13 | 3.0 | 7.1 |
|  | 20 | 3.0 | 183.9 |
| 3 Days | 5 | 3.0 | 26.7 |

TABLE 3c

Cardiac Transplant USA Trial
IL-6/Patient 1/2

| Days Post-Treatment | Days on Study | Baseline Value (ng/ml) | Post-Treatment Value (ng/ml) |
|---|---|---|---|
| 0 Days | 29 | 55.2 | 71.1 |
|  | 43 | 55.2 | 6.6 |
|  | 57 | 55.2 | 13.2 |
|  | 85 | 55.2 | 5.6 |
| 1 Day | 7 | 55.2 | 7.9 |
|  | 72 | 55.2 | 13.4 |
| 2 Days | 13 | 55.2 | 80.2 |
|  | 20 | 55.2 | 30.4 |
| 3 Days | 5 | 55.2 | 93.4 |

Table 2 depicts the expression of cytokines at baseline, prior to photopheresis therapy, and after a 2-day cycle of photopheresis therapy. Cytokine levels are depressed immediately post treatment.

Table 3 (panels a, b and c) illustrate the affect of photopheresis, after administration, on cytokine expression. From baseline, there is a significant up-regulation of cytokine expression. The expression is greater as the time from the administration increases.

Photopheresis modulates the function of cytokine expression in patients after receiving a cardiac transplant.

Bibliography

1. Edelson R L. Photopheresis: a clinically relevant immunobiologic response modifier. [Review] *Ann NY Acad Sci.* 191; 636:154–64.
2. Edelson R, Berger C, Gasparro F. et al. Treatment of cutaneous T cell lymphoma by extracorporeal photochemotherapy: Preliminary results. *N Engl J Med* 1987;316:297–303.
3. Malawista S, Trock D, Edelson R. Treatment of rheumatoid arthritis by extracorporeal photochemotherapy: a pilot study. *Arthritis Rheum* 1991;34:646–54.
4. Rook A.H, Freundlich B, Jegasothy B.V, et al. Treatment of systemic sclerosis with extracorporeal photochemotherapy: Results of a multicenter trial. *Arch Dermatol* 1992;128:337–46.
5. Rossetti et al., 1995, Transplant, 59:1, pp.149–151.
6. Investigator's Brochure for A Comparison Study of the Use of Extracorporeal Chemotherapy (ECP) With and Without Alpha Interferon in Treatment of Patients with Chronic HCV. June, 1996.
7. Publication of the American Liver Foundation Hepatitis C risk factors: Number of people with Hepatitic C at peak, but annual infection rate has dropped. *Progress* 1994–95; Volume 16, Nos. 1 and 2: 6.
8. Dienstag J L. Non-A, non-B hepatitis. Recognition, epidemiology, and clinical features. Gastroenterology 1983; 85:439–62.
9. Koretz R L, Stone O, Mousa M, Gitnick G L. Non-A, non-B post-transfusion hepatitis- a decade later. Gastroenterology 1985; 88:1251–4.
10. Choo Q-L, Ko G, Weiner A J, Overby L R, Bradley D W, Houghton M. Isolation of a cDNA derived from a blood-borne non-A, non-B viral hepatitis genome. *Science* 1989; 244:359–362.
11. Choo Q-L, Richman K H, Han J H, Berger K, Lee C, Dong C, Gallegos C, et al. Genetic organization and diversity of the hepatitis C virus. *Proc Natl Acad Sci* 1991; 88:2451–5.
12. Houghton M, Weiner A, Han J, Kuo G, Choo Q-L. Molecular biology of the hepatitis C viruses: Implications for diagnosis, development and control of viral disease. *Hepatology* 1991; 14:381–388.
13. Simmonds P, Holmes E C, Cha T-A, Chan S-W, McOmish F, Irvine B, et al. Classification of hepatitis C virus into six major genotypes and a series of subtypes by phylogenetic analysis of the NS-5 region. *J Gen Virol* 1993; 74:2391.
14. Shimizu Y K, Wiener A J, Rosenblatt J, Wong D C, Shapiro M, Popkin T, Houghton M, et al. Early events in hepatitis C infection of chipanzees. *Proc Natl Acad Sci* 1990:87:6441–4.
15. Garson J A, Ring C, Tuke P, Tedder R S. Enhanced detection by PCR of hepatitis C virus RNA. *Lancet* 1990; 336:878–9.
16. Kanai K, Iwata K, Nakao K, Kako M, Okamato H. Suppression of hepatitis C virus RNA by interferon-alpha. *Lancet* 1990; 336:245.
17. Weiner A J, Geysen H M, Christopherson C, Hall J E, Mason T J, Saracco G, et al. Evidence for immune selection of hepatitis C virus (HCV) putative envelope glycoprotein variants: Potential role of chronic HCV infections. *Proc Natl Acad Sci* 1992; 89:3468–72.
18. Shirai M, Akatsuka T, Pendleton C D, Houghten R, Wychowski C, Mihalik K, et al. Induction of cytotoxic T cells to a cross-reactive epitope in the hepatitis C virus nonstructural RNA polymerase-like protein. *J Virology* 1992; 66:4098–106.
19. Zignego A L, Macchia D, Monti M, Thiers V, Mazzetti M, Foschi M, et al. Infection of peripheral mononuclear blood cells by hepatitis C virus. *J Hepatology* 1992; 15:382–6.
20. Medoza, E C, Paglieroni, T G, Zeldis J B. Decreased phorbol myristate acetate- induced release of tumor necrosis factor-α and interleukin-1α from peripheral blood monocytes of patients chronically infected with hepatitis C virus. [In press]. Jour. of Inf. Diseases
21. Quian C, Camps J, Maluenda M D, Civeira M P, Prieto J. Replication of hepatitis C virus in peripheral blood mononuclear cells: Effect of alpha-interferon therapy. *J of Hepatology* 1992;6:380–3.
22. Cambell C, Dailley P J, Urdea M S, Wilber J, Collins M A, Mason A L, et al. HCV RNA in peripheral blood mononuclear cells: Effect of alpha-interferon therapy. *J of Hepatology* 1992; 16:380–3.
23. Gil B, Qian C, Riezu-Boj J I, Civeira M P, Prieto J. Hepatic and extrahepatic HCV RNA strands in chronic hepatitis C: different patterns of response to interferon treatment. *Hepatology* 1993; 18:1050–4.
24. Edelson R L. Photopheresis: a clinically relevant immunobiologic response modifier. [Review] *Ann NY Acad Sci.* 191; 636:154–64.
25. Vowels B R, Cassin M, Boufal M H, et al. Extracorporeal photochemotherapy induces the production of tumor necrosis factor-alpha by monocytes: Implications for the treatment of cutaneous T cell lymphoma and systemic sclerosis. *J Invest Dermatol* 1992;98:686–92.

What is claimed is:

1. A method, comprising:
a) administering a photoactivatable compound to the blood of a patient wherein said patient has an infectious disease of mononuclear blood cells, other than a retroviral infection,
b) treating at least a portion of said patient's blood of step a) with light in a wavelength that activates said photoactivatable compound, and
c) administering at least a portion of said patient's blood from step b) to said patient.

2. The method of claim 1 wherein said mononuclear blood cells are, infected with a non-viral pathogenic agent selected from the group consisting of parasites, bacteria and fungi.

3. The method of claim 1 wherein said photoactivatable compound is 8-methoxypsoralen.

4. A method, comprising:
   a) administering a photoactivatable compound to the blood of a patient wherein said patient has a chronic viral infectious disease, other than a retroviral infection,
   b) treating at least a portion of said patient's blood of step a) with light in a wavelength that activates said photoactivatable compound, and
   c) administering at least a portion of said patient's blood from step b) to said patient.

5. The method of claim 4 wherein said virus is CMV or HCV.

6. The method of claim 4 wherein said psoralen compound is 8-methoxypsoralen.

7. A method, comprising:
   a) administering a photoactivatable compound to the blood of a patient wherein said patient has an acute viral infectious disease, other than a retroviral infection,
   b) treating at least a portion of said patient's blood of step a) with light in a wavelength that activates said photoactivatable compound, and
   c) administering at least a portion of said patient's blood from step b) to said patient.

8. The method of claim 7 wherein said virus is CMV or HCV.

9. The method of claim 7 wherein said photoactivatable compound is 8-methoxypsoralen.

* * * * *